United States Patent
Staples et al.

(10) Patent No.: US 6,267,929 B1
(45) Date of Patent: Jul. 31, 2001

(54) TEXTURED SURFACE FOR TEST SAMPLE CARDS

(75) Inventors: John L. Staples, Florissant, MO (US); William L. DiMieri, Pittsburgh, PA (US)

(73) Assignee: Bio Mérieux, Inc., Hazelwood, MO (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/931,647

(22) Filed: Sep. 16, 1997

(51) Int. Cl.⁷ ............................... C12M 1/24; B01L 3/00
(52) U.S. Cl. ..................... 422/102; 156/153; 435/305.3; 435/305.4; 435/304.2; 435/288.5
(58) Field of Search ............................. 156/153; 422/58, 422/102–104; 435/288.5, 304.2, 305.3, 305.4

(56) References Cited

U.S. PATENT DOCUMENTS

| | | |
|---|---|---|
| 4,038,151 | 7/1977 | Fadler et al. . |
| 4,116,775 | 9/1978 | Charles et al. . |
| 4,118,280 | 10/1978 | Charles et al. . |
| 4,318,994 | 3/1982 | Meyer et al. . |
| 4,717,324 | 1/1988 | Schad et al. ........................ 425/130 |
| 5,345,052 | 9/1994 | Puddephatt ........................ 219/69.17 |
| 5,425,596 * | 6/1995 | Steere et al. ........................... 404/14 |
| 5,609,828 | 3/1997 | O'Bear et al. . |

FOREIGN PATENT DOCUMENTS

| | | |
|---|---|---|
| 0178907 | 10/1985 | (EP) . |
| 0290125 | 3/1988 | (EP) . |
| 0745856 | 12/1996 | (EP) . |

OTHER PUBLICATIONS

Shields, Adhesive Handbook, CRC Press, pp. 244–249, 1970.*
Harper, Handbook of Plastics, Elastomers, and Composites, pp. 9.47–9.52, 1992.*
Moser, Harry. (1995) "When Do You Need EDM?" *Modern Machine Shop* pp. 62–71.
Rhoades, Lawrence. (1996) "Understanding EDMed Surfaces." *Cutting Tool Engineering* pp. 22–31.
Weick, Peter. (1994) "When to Use Hot Runners in Flexible Manufacturing." *Modern Plastics* pp. 59 et seq.
The Society of Plastics Industry, Inc., (Date Unknown) *Mold Finish Size Reference Sheet.*
Snyder, Merle R., (Dec. 1994) "Benefits of hot runners can justify the initial cost." Modern Plastics pp. 53–57.
Husky Article., (Date Unknown) Husky Injection Molding Systems Brochure, "Hot Runner Systems".

* cited by examiner

*Primary Examiner*—Lyle A. Alexander
(74) *Attorney, Agent, or Firm*—McDonnell, Boehnen, Hulbert & Berghoff

(57) ABSTRACT

A test sample card is produced from a mold machined in accordance with an electronic discharge machining (EDM) process, with a resulting finely textured surface of the mold left intact. The mold produces a test sample card that has an even finely textured surface which improves the adhesion of a membrane to the card surface. The card is better able to withstand prolonged incubation periods without separation of the adhesive membrane from the card surface, as compared to prior art cards.

15 Claims, 5 Drawing Sheets

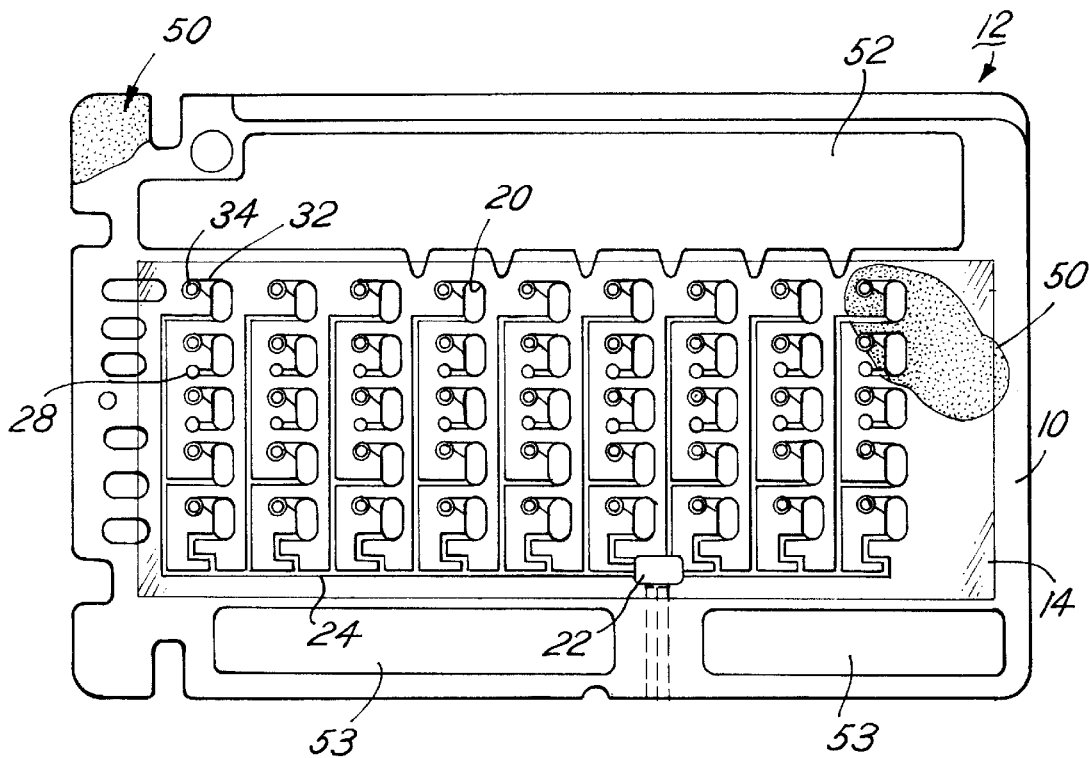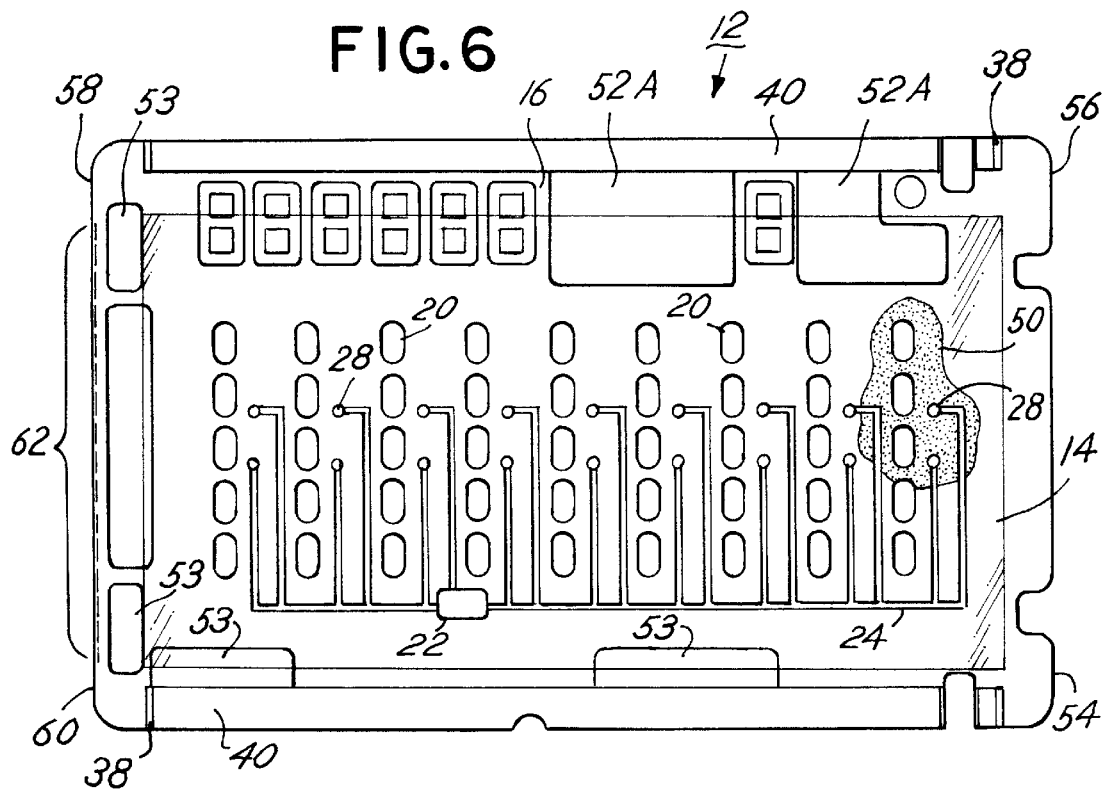

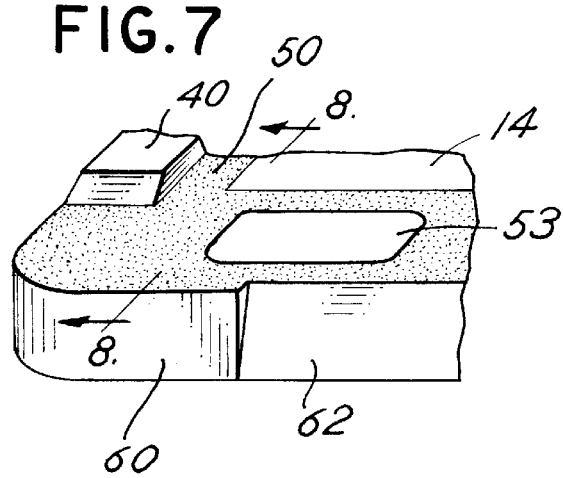
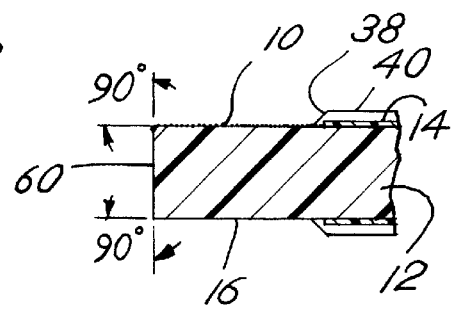
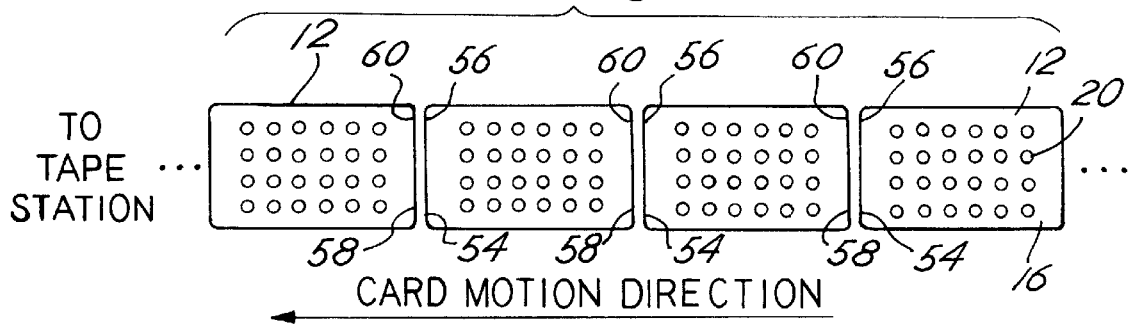
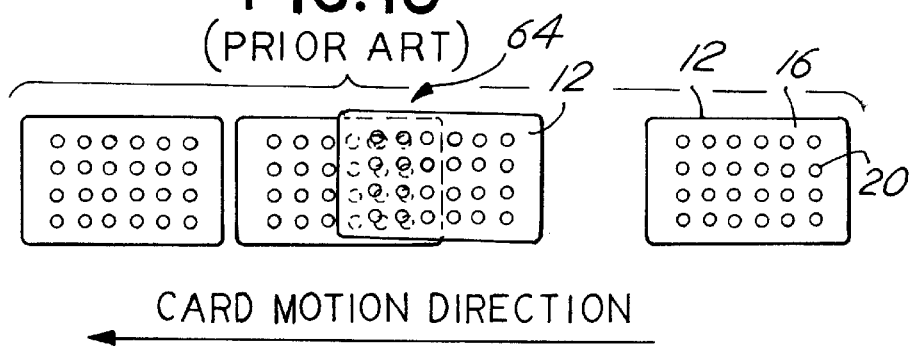

TEXTURED SURFACE FOR TEST SAMPLE CARDS

BACKGROUND OF THE INVENTION

A. Field of the Invention

This invention relates generally to the field of biological sample testing apparatus and systems, and more particularly to the subject of test sample cards which have one or more wells and fluid distribution channels formed therein for receiving a fluid or test sample containing a microbiological agent (such as a microorganism) and a reagent. The invention also relates to the subject of molds that are used to manufacture such devices.

B. Description of Related Art

A variety of test sample cards are described in the patent literature which have a well or reaction site for receiving a fluid sample containing a microbiological agent, such as a microorganism, and a reagent. The fluid sample is conveyed from a sample intake port to the well via fluid distribution channels formed in the surface of the card. Several representative patents include Meyer et al., U.S. Pat. No. 4,318, 994, Charles et al., U.S. Pat. No. 4,116,775; Fadler et al., U.S. Pat. No. 4,038,151, Charles et al., U.S. Pat. No. 4,118,280, and O'Bear et al., U.S. Pat. No. 5,609,928, the contents of each of which are fully incorporated by reference herein. These patents describe a test sample card having a plurality of wells arranged in the test sample card body. The reagent is typically loaded in the wells of the card during the completion of manufacture of the card. The reagent typically comprises a growth medium for a microbiological agent in a fluid or test sample. It is known to load a different reagent in each of the wells of the card in order to perform identification testing of a fluid sample containing an unknown microbiological agent or organism. It is also known to use the cards to test the microbiological agent for susceptibility to antibiotics by loading various antibiotic reagents into the wells.

It is known in the art to apply a transparent adhesive membrane to at least the front and usually the rear opposite surfaces of the card in a manner so as to cover the wells and fluid distribution channels that connect a fluid intake port of the card to the wells. The transparent adhesive membrane prevents the reagent from being dislodged from the well during shipping and handling and serves as a liquid barrier to prevent the fluid sample introduced into the well from leaking around the edges of the well.

In the sample testing system described in the Charles et al '280 patent, after the well of the test sample card has been loaded with the fluid sample at the time of use, the card is incubated for a period of time to promote a reaction between the microorganism and the reagent, i.e., growth of the microorganism. The well is periodically subject to optical analysis by a transmittance light source and a detector which are positioned on opposite sides of the well, or by alternate detection methods. If the growth medium or reagent is specifically suited for or "matches up" with the particular microorganism in the fluid sample, the population of the microorganism increases substantially, or some other predetermined reaction, i.e., chemical reaction, takes place, which results in the well turning cloudy and thus having a change in light transmission characteristics. The detector determines the amount of light that is transmitted from the source through the well and the adhesive membranes covering the well. By comparing the transmittance measurements over a period of time, typically several hours at least, with an initial transmittance measurement, it is possible to determine whether in fact the reagent and microbiological agent are matched by virtue of the change in transmittance measurement reaching a threshold value, such as twenty five (25) or thirty (30) percent. The change in light transmission characteristics therefore can be used to indicate the presence of a specific microorganism in the well. Identification and susceptibility may also be detected by absorbency measurements where a fluorescent agent is provided in the growth medium.

Some microorganisms require a relatively long period of incubation time, such as up to 18 hours, in order for the reaction characteristics in the well to change sufficiently to produce a test result using transmittance analysis. Localized or partial detachment of the transparent adhesive membrane from the surface of the test sample card has been occasionally observed during such prolonged incubation. This in turn can cause two deleterious effects: (1) leaking of the fluid out of one well into another well resulting in cross-contamination between wells, and (2) the admission of air into the wells, interfering with the transmittance measurement. Both effects compromise the integrity of the microbiological sample testing process.

The present inventors have discovered that the problem of inadequate tape adhesion during incubation can be traced to the molding process by which the cards are formed during manufacture, and can be overcome by replacing prior art molding techniques with new molding techniques, described in detail herein. In order to appreciate this aspect of the invention, some background on molding of test sample cards may be useful to the general reader.

Basically, in the prior art the test sample cards are formed in a steel mold using conventional plastic molding techniques. Steel pins and positive surface features in the mold create the test sample wells, fluid channels, bubble traps, and other features in the test sample cards. It has been conventional in the prior art to polish the interior surface of the card mold by hand with a polishing tool in order to produce an extremely smooth mold surface. A smooth mold surface was generally necessary in order for the test sample card to be released from the mold.

Hand polishing of the mold in the space immediately adjacent to the pins and other features is particularly difficult, and essentially impossible to control with precision, since the human hand is virtually incapable of operating a polishing tool in exactly the same manner (e.g., with the same amount of pressure or for the same amount of time) over a relatively large and complex surface, such as a mold for a test sample card. For example, there may be inadequate room for the hand tool to polish immediately adjacent to the pins forming the test sample card in a uniform manner. One portion of the mold surface adjacent to the pin may be relatively easy to polish, but the portion opposite the pin may be very difficult to polish with the polishing tool. As another example, the operator of the tool may be unable to polish the mold evenly around the positive features forming the fluid distribution channels, due to space considerations, polishing tool size and shape constraints, and the operator's desire to avoid accidentally polishing (and therefore altering) the extremely fine positive fluid channel features in the mold.

The inventors have discovered that the result of the prior art hand polishing technique is that small surface contours (such as localized low spots and localized high spots) are unintentionally formed in the card in the vicinity of the wells and fluid distribution channels. These features are not generally visible to the naked eye, but are readily apparent under magnification. These surface imperfections negatively impact the adhesion of the transparent membrane to the test sample well by creating small gaps or spaces between the membrane and the card surface. These gaps can potentially become the site of localized separation of the membrane from the card surface in conditions of prolonged incubation sufficient to cause cross contamination between wells, the formation of air bubbles in the wells, or other intolerable conditions. Additionally, hand polishing the mold is an expensive, time consuming and difficult human process that is inherently unsuited for the requirements of test sample card molding technology.

In a primary aspect of the invention, the present inventors have invented a test sample card, mold and process for manufacturing the test sample card that substantially avoids these problems by providing features that promote a better adhesion of the transparent adhesive membrane to the test sample card than achieved in prior art test sample cards. Moreover, the invention completely avoids precision hand polishing of the mold in the parts of the card where surface contours are critical to tape adhesion.

Accordingly, an object of the invention is to provide a test sample card which has features promoting the improved adhesion of a transparent membrane to the card to thereby enable the card to be subject to incubation without detachment of the adhesive membrane from the surface of the card.

A further object of the invention is to provide a mold for manufacturing test sample cards which has a surface texture that provides a finish on the surface of the test sample card that has improved properties for adhering a membrane to the surface of the card.

Another object of the invention is to provide a mold for manufacturing a test sample cards that provides substantially flat, textured and uniform surfaces around the test sample wells and channel features, thereby promoting adhesion of the membrane to the surface of the card. A still further object of the invention is to provide improving molding techniques, including hot runner and valve gate techniques, in the process of molding the test sample card.

These and other objects, advantages and features of the invention will be more apparent from the following detailed description of a preferred and alternative embodiments of the invention.

SUMMARY OF THE INVENTION

A test sample card is provided comprising at least one sample well and a card surface adjacent to the one sample well. The card surface has applied thereto an adhesive membrane for covering the sample well. The test sample card is formed with a finely textured surface in the card surface adjacent to the sample well, whereby the adhesion properties of the adhesive membrane to the card surface may be improved. The finely textured surface is preferably formed on the card surface by the action of molding the test sample card in a mold having a mold surface corresponding to the finely textured surface. The inventors have appreciated that a mold surface formed for example by an EDM (electrical discharge machining) process and left intact in critical areas surrounding the sample wells and fluid distribution channels, which results in a textured mold surface in these areas, is a preferred embodiment. The textured mold surface forms a finely textured surface on the test sample card. The EDM machined mold surface is left intact, that is, it is not hand polished as in the prior art, in the portion of the mold that forms the card surface adjacent to the sample wells and/or the fluid distribution channels.

In an embodiment in which the test sample card comprises front and rear opposite flat surfaces and a plurality of sample wells formed in the front and rear opposite surfaces, the finely textured surface is formed in both the front and rear parallel flat surfaces. The adhesive membrane is applied to both the front and rear opposite flat surfaces.

The above technique of forming a finely textured and uniform surface in the card surface adjacent to the well may also be used to apply a finely textured surface in the card surface adjacent to a fluid distribution channel connecting a fluid intake port in the card with the sample well. This promotes improved adhesion of the adhesive membrane to the test sample card to better seal the fluid distribution channels.

Improved handling characteristics for the card may be achieved by forming first and second edge regions in the mold for forming first and second opposite ends of the test sample card. The first and second opposite ends of the test sample cards comprise substantially square edges orthogonal to the front and rear opposite flat surfaces. These square edges prevent the cards from riding up over each other during processing of the cards in an assembly line, preventing splashing of reagents in the sample wells.

Improved test sample card manufacturing techniques are provided, including forming the finely textured surface in the mold and leaving this surface intact so as to form a textured surface in the test sample card. Additionally, utilizing a hot runner and valve gate approach to molding the test sample cards has resulted in a number of manufacturing advantages.

BRIEF DESCRIPTION OF THE DRAWINGS

A presently preferred embodiment of the invention is described below in conjunction with the appended drawing figures, wherein like reference numerals refer to like elements in the various views, and in which:

FIG. 5 is a plan view of the front surface of still another embodiment of the test sample card of FIG. 1;

FIG. 6 is a plan view of the rear surface of the test sample card of FIG. 5;

FIG. 7 is a detailed perspective view of the left hand edge of the card of FIG. 3;

FIG. 8 is a cross-sectional view of the left hand edge of the card of FIG. 3;

FIG. 9 is a perspective view of a portion of an assembly line for finishing the manufacture of the test sample cards, showing how the end features shown in FIGS. 7 and 8 prevent a phenomenon referred to as "shingling" from occurring; and FIG. 10 is an illustration of the "shingling" phenomenon which is substantially avoided with the square end features of the card shown in FIGS. 7 and 8.

DETAILED DESCRIPTION OF THE PREFERRED EMBODIMENTS

Figure 1:
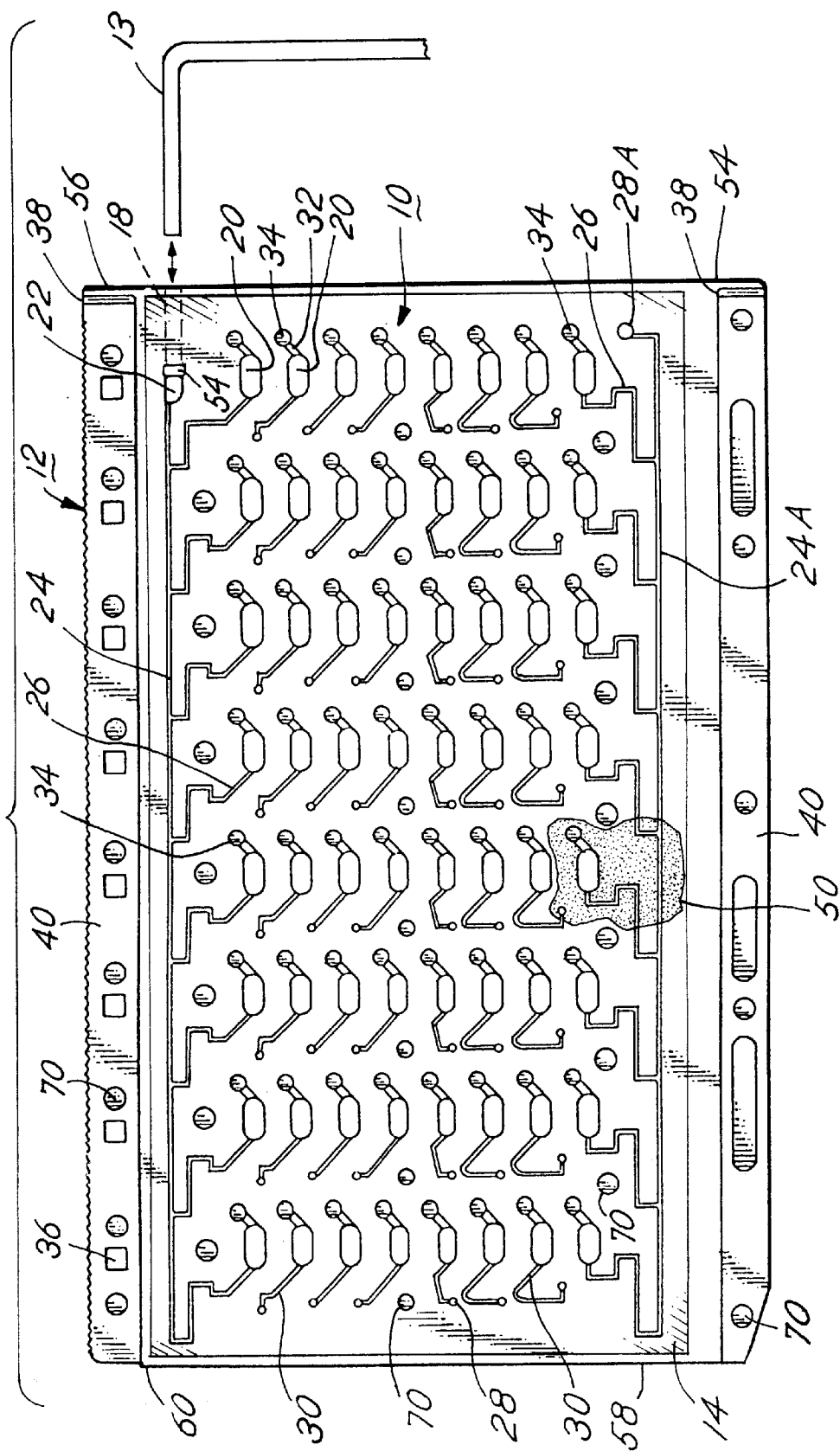
FIG. 1 is a plan view of the front surface of a test sample card incorporating features for improving the adhesion of a transparent membrane to the test sample card.
Figure 2:
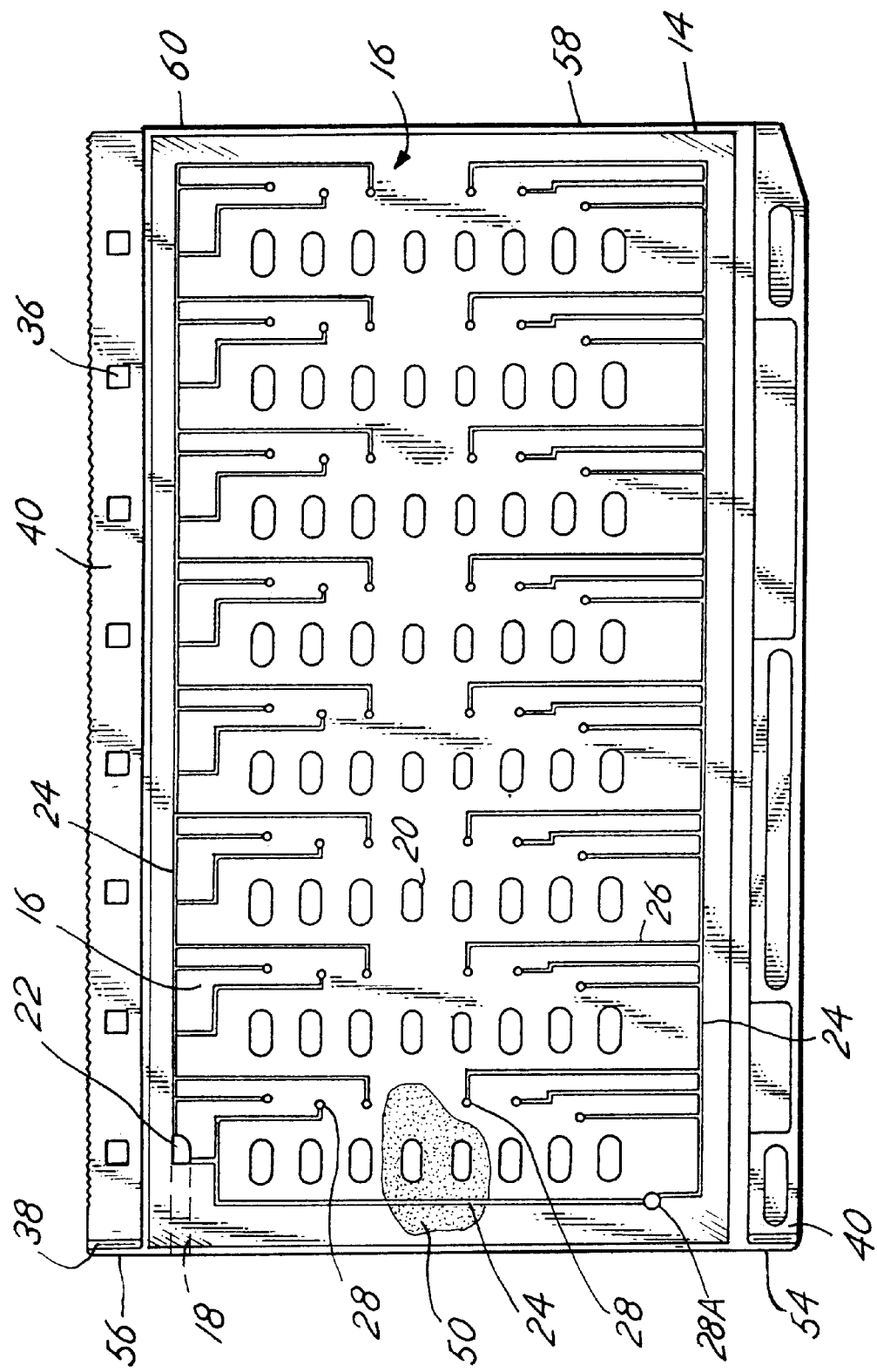
FIG. 2 is a plan view of the rear surface of the test sample card of FIG. 1.

Referring now to FIG. 1, the front surface 10 of a test sample card 12 is shown in a plan view. The test sample card 12 incorporates the present surface features for improving the adhesion of a transparent adhesive membrane 14 to the front surface 10 to the test sample card 12. FIG. 2 is a plan view of the opposite rear surface 16 of the test sample card 12 of FIG. 1, which also has the surface features for improving the adhesion of a transparent adhesive membrane 14 to the rear surface 16.

Before discussing the surface features of the card 10 for improving the adhesion of the membrane per se, other features of the test sample card that are apparent in FIGS. 1 and 2 will be addressed briefly. The test sample card 12 includes a plurality of sample wells 20 arranged in a preferred embodiment in an array of rows and columns of wells. The wells are formed in the mold by the presence of steel pins, with the molten plastic card material in the mold flowing around the pins to define the card 12 body and card surfaces adjacent to the pins. After the card is ejected from the mold and cooled, subsequent manufacturing procedure takes place in which the adhesive membrane 14 is applied the card surface 10, the wells 20 are pre-loaded with reagents and/or growth media for fluid or test samples, tape is applied to surface 16, a drying operation takes place, and the manufacturing process is complete.

At the time of use, the fluid or test sample is loaded into the prepared card 12 (after completion of all manufacturing and tape application steps) by means of vacuum loading techniques known in the art. Basically, one end of a straw-like transfer tube 13 is inserted into the fluid intake port 18 and secured in place, and the other end of the transfer tube 13 is placed into a receptacle, such as a test tube, containing the fluid sample. The fluid is drawn through the transfer tube 13 to an intake manifold 22 (also formed by a pin in the mold) that supplies fluid distribution channels 24 positioned on both the front and rear surfaces of the test sample card body. The fluid distribution channels 24 are formed by positive ridge elements in the surface of the mold. The fluid is carried along and within the fluid channels 24 to secondary supply channels 26 that lead to the sample wells 20. Through-card fluid distribution channels 28 and 28A (formed by pins in the mold) are provided for supplying fluid from the rear supply channels to well supply channels 30 and fluid distribution channel 24A, respectively, on the front surface 10 of the card 12.

The sample wells 20 are in communication with bubble trap passages 32 that convey any air bubbles that may form in the well to a respective bubble trap 34 (FIG. 1). Any air bubbles that may be present in the wells (either by virtue of a chemical reaction in the wells or carried to the wells as a result of vacuum loading) tend to migrate to the bubble traps 34, either by virtue of manual jiggling of the card or as a consequence of jostling or tumbling of the card during processing or incubation of the card in an analytical instrument.

The wells 20, bubble traps 34, sensor stop holes 36, and many other features, such as the ramp 38 and raised rail features 40, that are not specifically related to the present membrane adhesion features for the test sample card 12 are described in greater detail in the issued patent to Raymond E. O'Bear et al., U.S. Pat. No. 5,609,828, assigned to the assignee of the present invention, which is fully incorporated by reference herein. Additionally, the preferred material for the membrane 14 per is described in the patent application of Patrick Chen et al., Ser. No. 08/455,404 filed May 31, 1995, now U.S. Pat. No. 5,800,778, which is also incorporated by reference. The reader is directed to the above '828 and '778 patents for a detailed discussion of these features and still other features of the test sample card 12.

Figure 3:
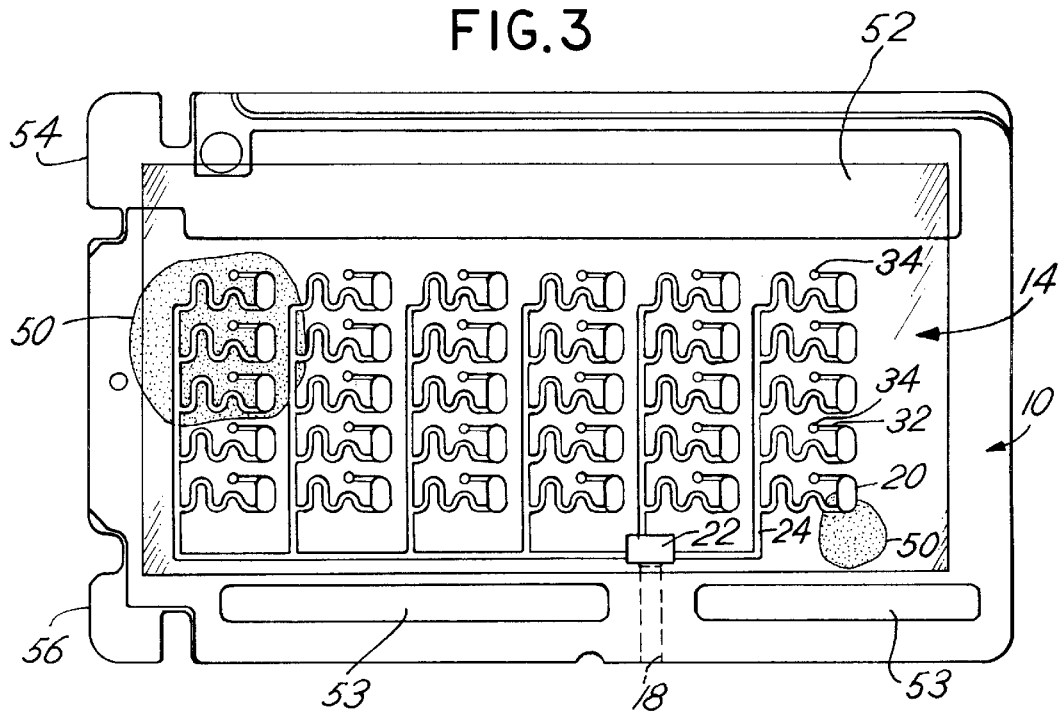
FIG. 3 is a plan view of the front surface of an alternative the test sample card of FIGS. 1 and 2 which also has the features for improving the adhesion of a transparent membrane to the test sample card.
Figure 4:
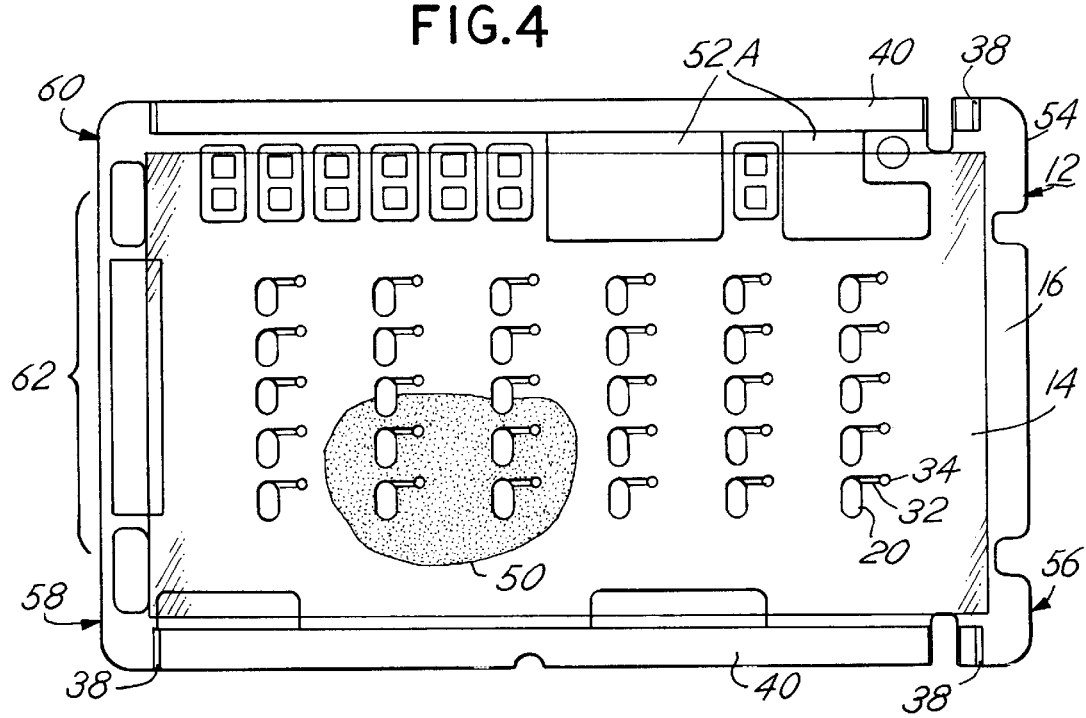
FIG. 4 is a plan view of the rear surface of the test sample card of FIG. 3.

An alternative test sample card is shown in FIGS. 3 and 4. Another alternative test sample card having the surface features of the present invention is shown in FIGS. 5 and 6. The same reference numerals used in FIGS. 1 and 2 also apply to like elements in FIGS. 3–6. The card of FIGS. 1–2 is particularly suitable for use in the sample testing machine described in the patent of Mark J. Fanning et al., U.S. Pat. No. 5,762,873, which is fully incorporated by reference herein. The test sample cards of FIGS. 3–6 are also suitable for use in the machine of the Charles et al. '280 patent discussed in the Background of the Invention section, commercially available from the assignee of the present invention. A more detailed description of the card shown in FIGS. 5 and 6, and various features not specifically related to the present invention, is found in the patent of John Staples, et al., U.S. Pat. No. 5,766,533, which is fully incorporated by reference herein.

The cards of FIGS. 1–6 have a finely textured surface 50 covering the front 10 and rear 16 surfaces of the test sample cards 12 in the region between the rails 40, instead of the totally smooth surface with localized high and low spots as found in prior art cards. Only a portion of the finely textured surface 50 is shown in FIGS. 1–6 (indicated by the stippling), it being understood that the remainder of the surface of the card 12 adjacent to the wells 20 and fluid distribution channels 24 between the rails 40 have the same textured surface. The finely textured surface 50 is visually observed on the test sample card surface as a matte-like finish. The textured surface is preferably an EDM twenty (20) micron finish, a plastics standard known in the art. The finely textured uniform surface 50 extends across the front 10 and rear 16 planar surfaces in the region where the adhesive membrane 14 is applied to the card. The finely textured surface 50 leads immediately adjacent to the sample wells 20 and the fluid distribution channels 24 of the card, which are covered by the adhesive membrane 14 during manufacture. It has been found that a flat, planar surface with the above textured characteristics advantageously promotes the adhesion of the membrane 14 to the test sample card 12 body.

The card of FIGS. 3–6 has recessed smooth areas 52 and 52A, for purposes of improving optical reading of identifying indicia on the card, and recessed smooth region 53. The mold surface forming these areas 52, 52A and 53 are finished smooth as a result of polishing the mold to improve release of the card 12 from the mold. These specific instances polishing of the mold do not require an exact amount of even polishing, since these regions 52, 52A and 53 are not immediately adjacent to the fluid distribution channels or the sample wells, and hence any separation of the adhesive membrane from the card in these regions 52, 52A and 53 will not affect the optical measurements of the wells or result in cross-contamination between wells. Additionally, these regions are located away from pin and other internal mold structures defining the wells and fluid distribution channels and thus the difficulties associated with manual mold polishing are not present with these areas.

The card of FIGS. 1 and 2 is preferably made from high impact polystyrene. The card of FIGS. 3–6 is preferably made from crystal polystyrene. Experiments have indicated that tape adhesion for these materials is generally better in the high impact polystyrene material. It has also been found that adhesion can be affected by the presence of a titanium dioxide coloring agent in the card material, which makes an otherwise translucent card appear white and opaque. This agent improves the adhesion strength in the crystal polystyrene material, but degrades adhesion in a high-impact polystyrene. For maximum adhesive results with these materials, a translucent high impact polystyrene material (without titanium dioxide) is indicated in the experimental data.

To achieve the finely textured surface 50 features of the test sample cards described above, we have found it advantageous to use a mold to impart this texture to the card, and more specifically to modify the mold used to manufacture the cards. Whereas in the prior art the mold was machined to the proper shape and then ground and polished to provide a smooth surface particularly in the area adjacent to the test sample wells and the fluid distribution channels, an expensive and difficult to control procedure as discussed above, we have discovered that superior surface features for the card are achieved by using the electrical discharge machining (EDM) process to form the surface contours in the mold for the test sample cards, particularly in the region corresponding the flat front 10 and rear 16 surfaces (FIGS. 1–6) where the wells 20 and fluid distribution channels 24 are formed and where adhesive tape 14 is applied to the front and rear card surfaces. Further, this mold surface in these areas is left intact and not polished, in contrast with the prior art technique of polishing.

In order for the general reader to better understand this aspect of the invention, a brief discussion of EDM machining is appropriate, although persons skilled in the art of machining are familiar with the technology and will readily comprehend this aspect of the invention. Briefly, EDM is a known machining technology, first develop many years ago, and which has now advanced to a level of fairly high precision. The EDM machining method uses a series of timed electrical pulses which are supplied to a nonstationary electrode to remove material from a workpiece. The electrical pules at the electrode produces a very high electric field, which results in a formation of plasma adjacent to the workpiece and an electrical discharge between the electrode and the workpiece. The discharge creates very high temperatures, causing localized melting of the workpiece material. When the current to the electrode is cut off, the sudden reduction in temperature causes melted material on the surface of the workpiece to be projected away from the workpiece, leaving a tiny crater. The melted material is redeposited on the workpiece adjacent to the crater or on a dielectric material associated with the electrode. A more detailed overview of the EDM process, and the resulting surface characteristics left behind on the workpiece in accordance with this process, is contained in two publications: Harry Moser, "When Do You Need EDM?" *Modern Machine Shop,* February 1995, pp. 62–71, and Lawrence Rhoades, "Understanding EDMed Surfaces", *Cutting Tool Engineering,* April 1996, pp. 22–31, the contents of both of which are fully incorporated by reference herein.

The EDM process results in a heat affected zone (HAZ) surface texture in the workpiece (i.e., mold in the present context). These surface characteristics consist of an essentially random distribution of small craters and globules of redeposited and recast material (the "recast layer"), and an annealed layer below that. The depth of the recast layer of the HAZ is proportional to the amount of current used in the EDM operation, but typically ranges between 0.00010 inches to 0.00040 inches. Because the EDM process works on the principle of melting, hardness of the underlying workpiece is not a constraint on the process, and indeed the process works well for hardened steel, tungsten carbide, and other similar materials suitable for molds.

In accordance with this aspect of the present invention, as noted above, the mold for the cards is machined using the EDM process, resulting in a HAZ and the associated surface characteristics discussed above. However, in an substantial departure from the prior art, the surface texture of the mold after the EDM machining has been performed that forms the card surface in the vicinity of the sample wells, fluid distribution channels, bubble traps and intake manifold is essentially left as is. No polishing, grinding, or other efforts are made to smooth the surface of the mold in these areas. (As noted above, some polishing may optionally be done in selected areas of the mold to improve release of the card from the mold, but these areas are preferably away from the above-referenced features where surface texture and resulting tape adhesion is critical). The particular depth of the surface characteristics in the mold may vary slightly within that provided inherently by the EDM process, in accordance with the invention, but uniform surface characteristics of the card in accordance with an EDM twenty (20) microns finish is a currently contemplated best mode for carrying out the invention.

The mold, with these surface characteristics, and specifically one in which hand polishing is not performed in the area corresponding to the card surface adjacent to the sample wells and fluid distribution channels and other areas critical to tape adhesion, thus produces a test sample card having a visually observable finely textured surface 50 on the front and rear surfaces of the card in the region where the adhesive membrane 14 is applied to the card surfaces 10 and 16. It has been discovered that this textured surface 50 results in a significantly improved surface for adhesion of the transparent membrane 14. Moreover, it has been found that the surface texture 50 does not contribute to cross-contamination between adjacent wells due to capillary action after the fluid has been introduced into the sample wells. More particularly, the depth of the surface texture 50 is sufficiently small that the adhesive applied to the bottom surface of the transparent membrane 14 fills in the craters and gaps in the surface of the test sample card, preventing cross-contamination.

Additionally, the EDM process for machining the mold helps insure that a flatter surface (in a more macroscopic sense) is formed in the card body around the well 20 and channel features 24 of the test sample card 12. As noted above, the prior art manual polishing procedures resulted in surface variations including localized low and high spots that can tend to cause release of the adhesive membrane after long incubation periods. Since the surface of the mold is machined using EDM, an automated process capable of substantial precision, localized low and high spots are substantially avoided. This promotes improved card adhesion properties, and the beneficial results, as discussed above.

In yet another aspect of the invention, the mold is designed such that the left and right side edges of the card in FIGS. 1–6 in regions 54, 56, 58 and 60 are formed substantially square or orthogonal to the front 10 and rear 16 surfaces of the test sample card. In the prior art, a draft angle of roughly four (4) degrees across the entire edge of the card was used in many test sample cards. This square feature is shown in more detail in FIGS. 7 and 8. The square edges 54, 56, 58, 60 of the card improves the handling and processing of the cards in an assembly line, where the cards are lined up single file with the left edge 54 and 56 of one card butting against the right edge 58, 60 of the adjacent card, as indicated in FIG. 9. More specifically, the square left and right edges, 54/56 and 58/60, respectively, of the test sample cards 12 reduces a tendency of the cards to ride up over each other in the assembly line into a disorderly, inclined, partially stacked condition indicated at 64 in the FIG. 10 (a phenomenon we have termed "shingling", due to the resemblance of the cards in this condition to the position of shingles on a roof). This promotes an ease of handling of the cards in the line, reduces labor, and helps the manufacturing line run at top speed.

Region 62 (FIGS. 3 and 7) between the square edges 58 and 60 may still have the small draft angle such as four (4) degrees to help with the ejection of the card from the mold, but this region slopes inwardly from the bottom corner of the card and is therefore region 62 is recessed relative to square regions 58 and 60. Hence, region 62 does not make contact with the edge of an adjacent card in a single file moving assembly line and cannot contribute to shingling. Rather, the square regions of adjacent cards butt against each other and do not have a tendency to ride up and over each other.

If the shingling occurs after the front surface 10 of the card 12 has had tape applied to it, and the reagent added to the wells 20 in the card, but before the rear surface 16 of the card has the tape applied, the shingling can cause a splashing of the reagents in the wells 20 and possible cross-contamination, by virtue of a reagent from one well being splashed into an adjacent 20 well in the card 12. Thus, the prevention of shingling achieved by the square edges 54, 56, 58, and 60 also helps insure the integrity of the entire testing process, since it helps eliminate one possible cause of inter-well contamination.

In a preferred implementation of the invention, a hot runner manifold with a valve gate system is used to mold the test sample cards in a system comprising a plurality (such as 8) identical molds. Hot runner molding systems, manifolds, and valve gates for such systems are described in the patent literature, and available from companies such as Husky Injection Molding Systems, Inc. of Bolton, Ontario Canada. An overview of hot runners is set forth in the article of Peter Weick, "When to Use Hot Runners in Flexible Manufacturing", *Modern Plastics* December 1994, pp. 59 et seq., incorporated by reference herein.

Basically, a hot runner system provides a heated flow channel and manifold to deliver the thermoplastic resin from a high temperature and pressure extruder to a nozzle at the proper temperature. The nozzle injects the molten material into the mold. Valve gate systems are a particular nozzle design that controls the flow of the thermoplastic resin through the nozzle and into the mold.

Conventional prior art molding techniques for test sample cards used a cold runner system and a tunnel gating system. Cold runner systems produce a connecting piece of scrap material known as a "cold runner", which requires some form of secondary handling such as grinding to remove the cold runner.

By adopting hot runner manifold and valve gate techniques for manufacturing the test sample cards, several advantages are obtained. First, the hot runner system permits the cooling cycle of the mold to be shortened, as compared to cold runner molding systems, because the extra time to solidify the heavy wall cold runner is not needed. Further, eliminating the cold runner allows the molder to not have to grind the test sample card and salvage and reuse the scrap material. Reuse of the ground material increases the threat of contamination of the mold material. The use of a hot runner system also reduces the added complication of an automation system for the molding process, because there is no cold runner being produced with the test sample cards.

The use of the hot runner and valve gate system also allows the molding equipment to get hotter material directly into the mold through the valve gate, which gives the molder a larger processing window to fill the cavity with more material. This in turn reduces shrink marks, warp, and weld lines in the finished test sample card. Valve gate systems allow the use of a larger gate to fill the mold more efficiently. When the fill cycle is complete and the valve is closed, it leaves very little sign of gating on the part.

Further, when molding polystyrene in a cold runner tunnel gating system into test sample cards, a large amount of material debris is generated and left on the face of the mold. This debris needs to be removed very often or mold damage is caused. The hot runner approach reduces the amount of maintenance and mold damage, which results in less down time due to maintenance and mold repairs.

The mold for the test sample cards uses a set of ejector pins to eject the test sample card from the mold. The ejector pins are in registry with the small circular ejector pin features 70 shown in FIG. 1. The ejector pins create a minute depression in the surface 10 of the test sample card 12 at the feature 70.

Thus, it will be appreciated from the foregoing description that there has been described a mold for manufacturing a test sample card 12 of the type in which an adhesive membrane 14 is applied to a card surface in a manner to cover a sample well 20 formed in the card. The mold comprises a mold body (that corresponds to the contours of the card) for forming the test sample card having a mold surface forming the front and rear card surfaces 10, 16 designated to have applied thereto the adhesive membrane 14 The mold surface is formed in the mold body according to an EDM machining process to produce a fine texture to the mold surface. The fine texture of the mold surface remains in the mold to thereby impart a finely textured surface 50 onto the card surface when the test sample card is molded in the mold.

In a preferred embodiment, the mold body further comprises first and second parallel opposed mold surfaces for forming respective front and rear surfaces 10 and 16 of the test sample card 12. The first and second parallel opposed mold surfaces are formed in the mold body in accordance with the EDM machining process to thereby produce a finely textured surface in the first and second parallel opposed mold surfaces, which impart finely textured front and rear surfaces of the test sample card.

In a preferred embodiment, the mold body further comprises at least one positive element (i.e., a ridge) formed on the surface of the mold for forming a fluid distribution channel (e.g., channel 24 in FIGS. 1–7) in the test sample card 12. The mold body has a surface adjacent to the positive element formed in accordance with the EDM machining process so as to produce a finely textured surface adjacent to the positive element. This promotes the adhesion of a adhesive membrane to the test sample card surface 50 adjacent to the fluid distribution channel 24.

The mold may also comprise at least one pin for forming the test sample well in the card. The mold body forms a surface adjacent to the pin in accordance with the EDM machining process to as to produce a finely textured surface 50 in the test sample card adjacent to the test sample well. A plurality of pins may be provided in the mold for forming a plurality of sample wells (such as shown in FIGS. 1–4) in the test sample card. The mold body further comprises a surface adjacent to each of said pins machined in accordance with the EDM machining process to as to produce a finely textured surface 50 in the test sample card and adjacent to the plurality of sample wells.

Besides from the illustrated embodiments, the invention is of course suitable for use with many other types of test sample cards, for example, the test sample cards described in the Background of the Invention section, supra, and in other similar types of devices. The particular details as to the number, size, shape and arrangement of sample wells, the configuration of the fluid distribution channels, and so on, is not particularly important to the inventive adhesive features described herein.

Persons of skill in the art will appreciate that variation may be made to the preferred and alternative embodiments described above without departure from the true spirit and scope of the invention. This true spirit and scope is determined by the appended claims, to be interpreted in light of the foregoing.

We claim:

1. A test sample card comprising at least one sample well for containing a fluid sample and a card surface adjacent to said at least one sample well, said card surface having applied thereto an adhesive membrane for covering said sample well, the improvement comprising:

said test sample card formed with a substantially flat and finely textured surface in said card surface immediately adjacent to and surrounding said at least one sample well as a consequence of the refraining from forming a smooth surface of a mold forming said test sample card in the area forming said card surface adjacent to said at least one sample well, whereby the formation of localized high and low spots in said card surface due to polishing said mold to form said smooth surface is prevented and the adhesion of said adhesive membrane to said card surface may be improved and the possibility of leakage of said fluid sample from said well or entry of air into said sample well may be reduced.

2. The improvement of claim 1, wherein said test sample card comprises front and rear opposite flat surfaces and a plurality of sample wells formed in said front and rear opposite surfaces, and wherein said finely textured surface is formed in both said front and rear parallel flat surfaces, and wherein an adhesive membrane is applied to both said front and rear opposite flat surfaces.

3. The improvement of claim 1, wherein said test sample card is molded in a mold using a hot runner molding system.

4. The improvement of claim 1, wherein said test sample card further comprises:

a substantially flat front surface and an opposite substantially flat rear surface, a first edge and an opposite second edge and first and second opposite side regions, said first and second edges and said first and second opposite side forming a rectangular peripheral edge of said test sample card, and wherein said first and second edges comprise square regions with respect to said front and rear surface of said test sample card such that said first and second edges are formed substantially orthogonal to said front and rear surfaces across the entire width of said first and second edges, whereby, when a plurality of said test sample cards are positioned in a single file moving assembly line, the tendency of one of said plurality of said test sample cards to ride over another of said test sample cards in said assembly line is substantially reduced.

5. The improvement of claim 1, wherein said test sample card is molded in a hot runner injection molding system.

6. The improvement of claim 1, wherein said finely textured surface is formed on said card surface by the action of molding said test sample card in a mold having a mold surface corresponding to said finely textured surface.

7. The improvement of claim 6, wherein said mold surface is formed by an Electrical Discharge Machining (EDM) machining process resulting in a textured mold surface, said textured mold surface forming said finely textured surface of said test sample card.

8. The improvement of claim 6, wherein said mold further comprises first and second edge regions forming first and second opposite ends of said test sample card, and wherein said test sample card comprises front and rear opposite flat surfaces, and wherein said first and second opposite ends of said test sample cards comprise substantially square edges orthogonal to said front and rear opposite flat surfaces, thereby improving the handling characteristics of said test sample cards.

9. A test sample card comprising at least one sample well for containing a fluid sample and a card surface having a fluid distribution channel formed therein for supplying a fluid sample to said at least one sample well, said card surface having applied thereto an adhesive membrane for covering said fluid distribution channel, the improvement comprising:

said test sample card formed with a substantially flat and finely textured surface in said card surface immediately adjacent to said fluid distribution channel as a consequence of the refraining from forming a smooth surface of a mold forming said test sample card in the area forming said card surface adjacent to said fluid distribution channel, whereby the formation of localized high and low spots in said card surface due to polishing said mold to form said smooth surface is prevented and the adhesion of said adhesive membrane to said card surface may be improved and the possibility of leakage of said fluid sample from fluid distribution channel or entry of air into said fluid distribution channel may be reduced.

10. The improvement of claim 9, wherein said test sample card comprises front and rear opposite flat surfaces and a plurality of sample wells formed in said front and rear opposite flat surfaces, and wherein said finely textured surface is formed in both said front and rear opposite flat surfaces, and wherein an adhesive membrane is applied to both said front and rear opposite flat surfaces.

11. The improvement of claim 9, wherein said test sample card is molded in a hot runner molding system.

12. The improvement of claim 9, wherein said test sample card is molded in a hot runner injection molding system.

13. The improvement of claim 9, wherein said finely textured surface is formed on said card surface by the action of molding said test sample card in a mold having a mold surface corresponding to said finely textured surface.

14. The improvement of claim 13, wherein said mold surface is formed by an Electrical Discharge Machining (EDM) machining process resulting in a textured mold surface, said textured mold surface forming said finely textured surface of said test sample card.

15. The improvement of claim 13, wherein said mold further comprises first and second edge regions forming first and second opposite ends of said test sample card, and wherein said test sample card comprises front and rear flat planar surfaces formed from front and rear flat planar mold surfaces, respectively, and wherein said first and second opposite ends of said test sample cards comprise substantially square edges orthogonal to said front and rear flat planar surfaces, thereby improving the handling characteristics of said test sample cards.

* * * * *